United States Patent [19]

Yoshioka et al.

[11] Patent Number: 4,855,405

[45] Date of Patent: Aug. 8, 1989

[54] GLUTAMATE RECEPTOR INHIBITOR

[75] Inventors: Masanori Yoshioka, Kyoto; Hidemitsu Hou, Osaka; Nobufumi Kawai, Tokyo, all of Japan

[73] Assignees: Tokyo Metropolitan Institute for Neurosciences, Tokyo; Takeda Chemical Industries, Ltd., Osaka, both of Japan

[21] Appl. No.: 59,517

[22] Filed: Jun. 8, 1987

Related U.S. Application Data

[63] Continuation of Ser. No. 707,381, Mar. 1, 1985.

[30] Foreign Application Priority Data

Mar. 2, 1984 [JP] Japan .................................. 59-38677

[51] Int. Cl.$^4$ ..................... C07K 15/00; A61K 35/56; A61K 37/02
[52] U.S. Cl. ................................ 530/300; 424/95; 514/2; 514/21; 514/17; 514/18; 530/344; 530/330; 530/331
[58] Field of Search ............... 530/300, 344, 330, 331; 424/95; 514/2, 21, 17, 18

[56] References Cited

U.S. PATENT DOCUMENTS 4,452,888   6/1984   Yamazaki et al. .................... 435/69

OTHER PUBLICATIONS

Brain Research, 247, 169–171, (1982), Kawai et al.
Central Patents Index, Basic Abstracts Journal Section B, Farmdoc, (1980).
Microelectrophoretic Investigations of Mammalian Central Transmitters (Aug. 25, 1983), Australia, Lecture Summaries, p. 4, Kawai et al.
Congress of the International Union of Physiological Sciences, (Aug. 29, 1983), Australia, Lecture Summaries, p. 89, Kawai et al.
Bochem. and Biophys. Res. Comm., 90, (1979), 1194–1200, Blank et al.
J. of Clinical Science, 17, No. 12, (1981), Masugi et al., (English transation), V–of Record in parent 707, 381.
Mandel et al., Advances in Biochemical Psychopharmacology, (1983), 37, pp. 227–221, "CNS Receptors—From Molecular Pharmacology to Behavior".
Abe et al., J. Physiol., (1983), 339, pp. 243–252, "Effects of a Spider Toxin on the Glutaminergic Synapse of Lobster Muscle".
Kawai et al., Chemical Abstratcs, 97, No. 11, Sep. 13, 1982, p. 255, No. 86723b, Columbus, Ohio, U.S., "Effect of a Spider Toxin on Glutaminergic Synapses in the Mammalian Brain", and Biomed. REs. 1982, 3(3), 53–5, Abstract.
Kawai et al., Brain Research, (1983), 278, pp. 346–349, "Blockade of Squid Giant Synapse by a Spider Toxin".

*Primary Examiner*—Howard E. Schain
*Attorney, Agent, or Firm*—Wegner & Bretschneider

[57] ABSTRACT

A novel glutamate receptor inhibitor obtained from Joro spider venom glands, and its manufacturing method.

6 Claims, No Drawings

GLUTAMATE RECEPTOR INHIBITOR

This application is a continuation of Ser. No. 707,381, filed Mar. 1, 1985.

This invention relates to a novel compound or its salt, having a glutamate receptor inhibitory action, and to its manufacturing method. The compound is contained in Joro spider (Nephila clavata) venom glands [A review on the glutamate receptor appears in H.M. Gerschenfeld, Physiological Reviews, vol. 53, pp. 1–92 (1973)].

Arthropods such as insects, when bitten by a Joro spider, are paralyzed and fall a victim to the spider. Therefore, it has long been believed that Joro spiders produce a substance that paralyzes the nerve-muscle systems of arthropods such as insects. Kawai, one of the inventors of this invention, using the nerve-muscle synapses of Palinusus japonicus walking legs, found a substance specifically blocking glutamate-activating synapses to be present in Joro spider venom glands [N. Kawai, A. Miwa and T. Abe, Brain Research, vol. 247, pp. 169–171 (1982); N. Kawai, A. Miwa, M. Saito and M. Yoshioka, Mircoelectrophoretic Investigations of Mammalian Central Transmitters (Aug. 25, 1983, Canberra, Australia) Lecture Summaries, p. 4; N. Kawai, A. Miwa, M. Saito and M. Yoshioka, 29th Congress of the International Union of Physiological Sciences (Aug. 29, 1983, Sydney, Australia) Lecture Summaries, p. 89; N. Kawai, 8th Conférence en Neurobiologie (Nov. 25, 1983, Gif, France) Lecture Summaries, p. 101. The inventors of this invention have now successfully isolated from Joro spider venom glands a substance specifically blocking glutamate-activating synapses as described in the above-mentioned literature and lecture summaries, and have found that the substance is a novel compound having a glutamate receptor inhibitory action, and have completed this invention after further studies.

So far, diethyl and dimethyl ester L-glutamate [H.V. Wheal and G.A. Kerkut, Comparative Biochemistry and Physiology, vol. 51C, pp. 79–81 (1975)], α-methyl ester L-glutamate [C. Lowagie and H.M. Gerschenfeld, Nature, vol. 248, pp. 533–535 (1974)]or L-proline [A. Van Harreveld, Journal of Neurobiology, vol. 11, pp. 519–529 (1980)]are compounds known to have inhibitory action on the glutamate receptor. While the above-described compounds show poor specificity and need no less than $10^{-3}$ M to exhibit inhibitory action, the purified spider toxin of this invention shows extremely specific and high glutamate receptor inhibitory activity even at concentrations as low as $10^{-3}$ M. The site of inhibitory action is the post-synaptic membrane. The action is irreversible and does not disappear even after washing with bioassay medium e.g. saline solution. This indicates that the inhibitor under this invention binds to the receptor far more strongly than any other known synthetic compounds. The utility of this inhibitor is thus very high, as it is useful for isolation research, structural analysis, local analysis and the like of the glutamate receptor.

Moreover, the inhibitor under this invention exerts a strong insecticidal action, showing excellent insecticidal effect at a concentration of 10 ppm against insects harmful to rice, tea, vegetables, fruits and the like. These harmful insects include rice-stem borers, green caterpillars, leaf-hoppers, skipper butterflies, oriental moths, powder moths, rice insects, aphids, tetranychids and the like. The previously mentioned review on the glutamate receptor states that these vermin possess the glutamate receptor; thus the insecticidal action of the inhibitor under this invention is thought to be based on glutamate receptor inhibitory action. As described hereinafter, the inhibitor, a water-soluble compound, is used primarily in aqueous solutions. The inhibitor is a natural substance and has low toxicity to humans, animals and fish than conventional insecticides such as organic phosphorus compounds, organic chlorine compounds, carbamates, pyrethrins.

The inhibitor may usually be obtained in the free form. The inhibitor may be converted to a salt in the course of extraction or purification or after isolation, according to the conventional method. Such a salt includes agriculturally or pharmaceutically acceptable base salt or acid-addition salt. As the agriculturally or pharmaceutically acceptable base salt, there may be used inorganic base salt or organic base salt. As the inorganic base salt, there may be used for example alkali metal salt (e.g. sodium salt, potassium salt) or alkali-earth metal salt (e.g. calcium salt). As the organic base salt, there may be used for example tri $C_{1-6}$ alkyl ammonium salt (e.g. triethyl-ammonium salt, tributyl ammonium salt) or salt with a cyclic tertiary amine (e.g. pyridinium salt). As the agriculturally or pharmaceutically acceptable acid addition salt, there may be used for example inorganic acid-addition salt (e.g. hydrochloride, sulfate) or organic acid-addition salt. As the organic acid-addition salt, there may be used for example carboxylic acid-addition salt (e.g. trifluoroacetate) or organic sulfonic acid-addition salt (e.g. methanesulfonate, p-toluenesulfonate).

The manufacturing method for obtaining the inhibitor under this invention is described below. The method comprises an extraction process and a purification process. The addition of a preliminary crushing process permits effective extraction.

(1) Crushing

Joro spiders or their venom glands are crushed. Venom glands are picked out from the spiders with a conventional manner e.g. using a pair of pincette. Crushing can be done either nonmechanically or mechanically. Ordinary atomizers and homogenizers as well as ultrasonic can be used for crushing. The ideal method is to put the entire spider body or venom glands alone into the solvent for the subsequent extraction process for ultrasonic crushing.

(2) Extraction

Extraction is carried out by using an extraction solvent. It is more advantageous to extract only the venom glands than the whole body of spiders. Water, a conventional electrolyte aqueous solution or a conventional organic solvent mixed homogeneously with water or the like can be used as the extraction solvent. Saline solution, ammonium chloride aqueous solution, sodium sulfate aqueous solution or the like can be used as the electrolyte aqueous solution. The concentration range of the solution to be used is 0 to 1.5% (W/V), preferably 0.3 to 0.9% (W/V). The organic solvent homogeneously miscible with water can be, for example, alcohol such as methyl alcohol or ethyl alcohol. Ideal as the extraction solvent is 0.3 to 0.5% (W/V) saline solution. The solvent must be added in the extraction process if crushing was done without solvent. On the other hand, if solvent was used in the crushing process, the solvent need not be added. Extraction can be carried out in accordance with a conventional method. It can be done by letting the mixture stand for a long time or it can be done in a short time using extraction machines. Ordinary stirrers, centrifuges and the like can be used in the extraction process as the extraction machine. Centrifugation is preferable because it allows easy separation of extract solutions and residues after extraction. Centrifugal velocity should be 1,000 to 100,000 rpm, lasting ten minutes to three hours to obtain the extract aqueous solution. The active component is identified by the bioassay method later described in detail, i.e., by recording the excitatory postsynaptic potential (EPSP) at the nerve-muscle synapses of Palinusus japonicus walking legs. The bioassay results reveal the active component is present in extract. The active component does not substantially transfer into ordinary organic solvents such as ethyl acetate and methylene chloride but remains in the aqueous phase.

(3) Purification

Macromolecular proteins should be removed from the above-mentioned aqueous extract solution by adding an acid to the extract and removing the precipitate that forms. The acid to be used here is, for example, perchloric acid, periodic acid, trichloroacetic acid or the like. The concentration of the acid used is 0.2 to 2 M. Acid addition must be continued till the precipitate ceases to form. The extract aqueous solution, deprived of macromolecular proteins, is then concentrated under reduced pressure and subjected to an ordinary purification process employing gel filtration, ion-exchange resin (a cation or anion), column chromatography, thin-layer chromatography for fractionation, high-pressure liquid chromatography or the like. The purification method using the ion-exchange resin e.g. anion-exchange resin and cation-exchange resin is preferable, since it so efficiently purifies as described below. When the concentrated aqueous solution mentioned above is passed through an anion-exchange resin column, impurities are absorbed by the resin while the active parts are recovered in the aqueous solution without being absorbed by the resin. When the aqueous solution containing the recovered active parts is passed through a cation-exchange resin column, the active component is absorbed by the resin. The elution of chromatography is carried out by the use of, for example, the above-mentioned electrolyte aqueous solution [e.g., 0.1 to 1.5% (W/V) saline solution]. DEAE-Cellulose, QAE-Sephadex, Dowex 1 x 8 and the like can be used as anion-exchange resin, while CM-Sephadex, Dowex 50W and the like can be used as cation-exchange resin. Purification via silica gel thin-layer for fractionation, for example, is performed as described below. When the aqueous solution containing the active component is spotted on "Silica gel 60 thin-layer plate (E. Merck AG)" and developed with, for instance, a phenol-water mixed solvent [3:1 (V/V)], the inhibitor that fluoresces with fluorescamine can be detected at the position of Rf value 0.20. By use of "Cellulose thin-layer plate (E. Merck AG)", the inhibitor can be detected at the position of Rf values 0.54 and 0.65, developed with phenol-water mixed solvent 3:1 (V/V) and n-propanol-water mixed solvent 7:3 (V/V) respectively. The aqueous solution containing the active component is then spotted on "Silica gel 60 thin-layer plate for fractionation (E. Merck AG)" and, after develpoment with the above-mentioned mixed solvent or the like, those portions corresponding to the inhibitor are scraped off and extracted with water to obtain an aqueous solution of the inhibitor. The inhibitor obtained here can be identified as a single spot by means of silica gel thin-layer chromatography, gel filtration, or electrophoresis. The purifed inhibitory contains subtantially no macromolecular protein which may act as an antigen to mammalians.

The inhibitor which is thus obtained from Joro spider venom glands has the following properties:

(1) Molecular weight is within the range of 500±200;
(2) It is substantially insoluble in ethyl acetate and soluble in water;
(3) The activity remains unchanged when heated to 80° C. for 20 minutes in water;
(4) The activity remains unchanged when heated to 80° C. for 20 minutes in 0.4 M perchloric acid;
(5) It shows in electrophoresis neutral electric charge with use of 0.01 M phosphate buffer (pH 7) and positive electric charge using 0.2 M formate buffer (pH 2.25);
(6) It develops color with ninhydrin and fluoresces with fluorescamine;
(7) It yields Rf values 0.20 on "Silica gel 60 thin-layer plate (E. Merck AG)" developed with phenol-water mixed solvent 3:1 (V/V), and 0.54 and 0.65 on "Cellulose thin-layer plate (E. Merck AG)" developed with phenol-water mixed solvent 3:1 (V/V) and n-propanol-water mixed solvent 7:3 (V/V) respectively;
(8) It shows maximum absorption at 270 nm, minimum absorption at 245 nm in water (pH 6.1).

Bioassay Method

The nerve-muscle synapses of Palinusus japonicus walking legs are used in testing the active component. Stretcher muscles of Palinusus japonicus walking legs are exposed to record the potential, using glass microelectrodes filled with 3 M potassium chloride. The activity of the inhibitory substance was determined by either (1) or (2) below:

(1) The excitatory nerve of the stretcher muscle is disected into a single axon and gives electric stimulation through a suction electrode. Excitatory nerve stimulations give rise to release glutamic acid, which binds to the glutamate receptor, resulting in the development of excitatory postsynaptic potential (EPSP) of 3 to 5 mV in the postsynaptic membrane. The glutamate receptor inhibitor suppressed the EPSPs irreversibly in a dose-dependent manner.

(2) A glass microelectrode filled with glutamic acid (1 M, pH 8), is positioned close to the nerve-muscle synapse. Inward current of about $1 \times 10^{-9}$ A to the microelectrode is used to eject glutamic acid electrophoretically. As a result, 3 to 5 mV depolarized potential (glutamate potential) is generated in the postsynaptic membrane, the potential being in proportion to the intensity of the current applied. The glutamate receptor inhibitor suppressed the glutamic acid potential irreversibly in a dose-dependent manner.

As mentioned above, the glutamate receptor inhibitor of this invention has excellent insecticidal activity. Thus, the present invention relates also to an insecticidal composition, which comprises an insecticidally effective amount of the inhibitor and carrier or carriers. The carriers may be agriculturally or horticulturally acceptable ones, such as a liquid carrier e.g. water, alcohols (e.g. methyl alcohol, ethyl alcohol), solid carrier e.g. mineral powders (such as clays such as kaolin, bentonite and acid clay), talc such as talc powder, silicas such as diatomaceous earth, alumina, activated carbon etc.

EXAMPLE 1

Crushing, Extraction

One g of venom glands obtained from 400 Joro spiders collected in Japan was put into an ultrasonic cleaner (Branson Cleaning Equipment Company, B-12) together with 5 ml of 0.3% (W/V) saline solution; after ten minutes of ultrasonic treatment, the mixture was centrifuged at 10,000 rpm for 30 minutes with a refrigerated centrifuge (Sakuma Seisakusho, 50A-1, Rotor 6B) to obtain a saline extract. Sediment obtained was reextracted twice as described above with 5 ml of 0.3% (W/V) saline solution. The supernatants obtained in the reextractions were combined to obtain the saline extract.

Note 1: Extraction was also performed with use of 0%, 0.9% and 1.5% (W/V) saline solutions in place of the above 0.3% (W/V) saline solution (other conditions are the same). Better extraction results were obtained with 0.3%, 0.9% and 1.5% (W/V) solutions than with 0% solution.

Note 2: One hundred $\mu$l of the supernatant was extracted three times with 100 $\mu$l of ethyl acetate. Extracts were combined and evaporated to dryness with nitrogen gas. The residues were dissolved in 0.3% (W/V) saline solution and then examined by the bioassay method described above. Glutamate receptor inhibitory activity was not observed which suggests that the inhibitor could not be transferred into ethyl acetate phase.

EXAMPLE 2

Purification with Sephadex G-10 Column (Gel Filtration)

The saline extract obtained in Example 1 was concentrated to 5 ml at 40° C. under reduced pressure. Five ml of the concentrate was applied and eluted with purified water (The Pharmacopoeia of Japan, 10th edition, 1981) on a Sephadex G-10 column (2.6 cm $\times$ 62 cm). Elution was performed at a 0.5 ml/min flow rate, and the eluate was collected in fractions of 5 ml each. Bioassay was performed by the method described above for fractions containing the active component. Elution of the active component was observed in fractions of 31 to 37.

EXAMPLE 3

Purification with CM-Sephadex C-25 Column

The fractions containing the active component obtained in Example 2 were concentrated and evaporated to dryness at 40° C. under reduced pressure, and were then dissolved in 0.8 ml of 0.1 M ammonium acetate buffer (pH 6). The solution was applied and eluted on a CM-Sephadex C-25 column (2.6 cm $\times$ 37 cm). The fractional collection was carried out as in Example 2. Fractions of 1 to 190 were first eluted with 0 to 1.0 M ammonium acetate buffer (pH 6, gradient), followed by elution with 2.0 M ammonium acetate buffer (pH 6). Elution of the inhibitor was observed in fractions of 212 to 230.

EXAMPLE 4

Detection with Thin-Layer Chromatography

The saline extract obtained in Example 1 and the active fractions obtained in Examples 2 and 3 were separately spotted on "Silica gel 60 thin-layer plate (E. Merck AG)" or "Cellulose thin-layer plate (E. Merck AG)" and developed with a phenol-water mixed solvent (3:1, V/V) or n-propanolwater mixed solvent (7:3, V/V). After the development, a substance that fluoresced with fluorescamine was identified as the inhibitor. The detection limit of the reaction with fluorescamine is $10^{-12}$ mole [H. Nakamura and J.J. Pisano, Journal of Chromatography, vol. 121, pp. 33 to 40 (1976)]. "Silica gel 60 thin-layer plate (E. Merck AG)" and "Cellulose thin-layer plate (E. Merck AG)" are commercially available prducts distributed by E. Merck AG.

EXAMPLE 5

Purification with Silica Gel Thin-Layer for Fractionation

The fractions obtained in Example 3 containing the active component were combined and, after concentration and evaporation to dryness at 40° C. under reduced pressure, were dissolved in 0.1 ml of water, spotted on "Silica gel 60 thin-layer plate for fractionation (E. Merck AG)", and developed with a phenol-water mixed solvent (3:1, V/V). After development, the inhibitor was scraped off and extracted with 1 ml of water. The extraction was carried out by letting stand for 15 hours the mixture of water and scraped silica gel containing the inhibitor. The supernatant was centrifugated at 3,000 rpm for five minutes and the resulting supernatant was concentrated in vacuo to 0.1 ml to obtain an aqueous solution of the inhibitor. This inhibitor obtained gave a single spot on the thin layer after the solution was spotted and developed as described in the purity test in Example 4. "Silica gel 60 thin-layer plate for fractionation (E. Merck AG)" is commercially available

EXAMPLE 6

Determination of the Molecular Weight

The molecular weight of the inhibitor was estimated as 500$\pm$200 by calculating the relative elution position on the Sephadex G-10 column in comparison of that of L-alanyl-L-lysyl-L-asparaginyl-L-phenylalanine (MW 625.78), glycyl-L-leucyl-L-tyrosine (MW 351.43) and thymidine (MW 181.19) which were used as markers. The elution conditions of the Sephadex G-10 column (2.6 cm $\times$ 62 cm) were as in Example 2.

EXAMPLE 7

Electrophoresis

To 100 $\mu$l of the saline extract obtained from extraction with 0.9% saline extract in Example 1 was added 25 $\mu$l of 2 M perchloric acid. The resulting mixture was allowed to stand at room temperature for 30 minutes and then centrifuged at 10,000 rpm for 15 minutes. The supernatant was separated and 50 $\mu$l of 1 M potassium hydrogen carbonate was added to it. Fifty microliter of the solution thus obtained was centrifuged at 3,000 rpm for five minutes. One $\mu$l of the supernatant was spotted on a cellulose acetate membrane (1 cm $\times$ 6 cm) and developed for two minutes in a 0.01 M phosphate buffer under under 0.5 mA of electric current per cm. After development, the membrane was cut at two-mm intervals and extracted for 15 hours with 50 $\mu$l of the bioassay buffer (The buffer was prepared in the following. Into 800 ml of purified water were dissolved 467 mmoles of sodium chloride, 10 mmoles of potassium chloride, 20 mmoles of calcium chloride, 8 mmoles of magnesium chloride and 2 mmoles of tris(hydroxymethyl)aminomethane. After mixing, the resulting solution was adjusted to a pH of 7.4 by adding hydrochloric acid and puified water was added until the total volume amounted to 1 liter.) The bioassay performed on inhibitor showed the same electrophoresis as ε-DNP-Lys, an electrophoretic marker, indicating the inhibitor to be neutral, its neutrality also being proven in electrophoresis performed in the same way on the purified product of the inhibitor obtained in Example 5. Under the acidic medium (0.2 M formate buffer pH 2.25) condition, the migration rate of the inhibitor obtained from examples 3 and 5 was two times higher than the electrophoretic marker, ε-DNP-Lys. This indicated that the inhibitor had positive charge in the condition employed. In the above, ε-DNP-Lys means ε-(2,4-dinitrophenyl)-L-lysine.

EXAMPLE 8

Bioassay of the Purified Product

After dissolving $10^{-10}$ mole of the purified product obtained in Example 5 in 100 μl of water to $10^{-6}$ M concentration, the aqueous solution was diluted successively, each dilution being 10-fold to prepare aqueous solutions of $10^{-7}$, $10^{-8}$. $10^{-9}$, $10^{-10}$ M concentrations. The bioassay performed by the above method revealed that the solutions showed glutamate receptor inhibitory activity up to $10^{-9}$ M concentration

What we claim is:

1. An insecticidally effective composition comprising a glutamate receptor inhibitor, said glutamate receptor inhibitor having insecticidal properties when present in a concentration of at least $10^{-9}$ M, said glutamate receptor inhibitor possessing only one single spot at the position of Rf value of substantially 0.20 on a Silica gel 60 thin-layer plate developed with phenol-water mixed solvent 3:1 (V/V), said glutamate receptor inhibitor being an organic compound obtained from Joro spider venom glands and which has the following properties:
   (a) molecular weight is within the range of 500±200;
   (b) it is substantially insoluble in ethyl acetate and soluble in water;
   (c) the activity remains unchanged when heated to 80° C. for 20 minutes in water;
   (d) the activity remains unchanged when heated to 80° C. for 20 minutes in 0.4 M perchloric acid;
   (e) it shows in electrophoresis neutral electric charge with use of 0.01 M phosphate buffer (pH 7) and positive electric charge using 0.2 M formate buffer (pH 2.25);
   (f) it develops color with ninhydrin and fluoresces with fluorescamine;
   (g) it shows maximum absorption substantially at 270 nm, and minimum absorption substantially at 245 nm in water (pH 6.1).

2. An insecticidal composition comprising an amount of the glutamate receptor inhibitor of claim 1 in a concentration of at least 10 ppm and an agriculturally or horticulturally acceptable carrier therefor.

3. A method of combatting insects which comprises contacting said insects with an insecticidal composition of claim 2.

4. A glutamate receptor inhibiting compound obtained from Joro spider venom glands, said compound possessing only one single spot at the position of Rf value of substantially 0.20 on a Silica gel 60 thin-layer plate developed with phenol-water mixed solvent 3:1 (V/V), said compound having the following properties:
   (a) molecular weight is within the range of 500±200;
   (b) it is substantially insoluble in ethyl acetate and soluble in water;
   (c) the activity remains unchanged when heated to 80° C. for 20 minutes in water;
   (d) the activity remains unchanged when heated to 80° C. for 20 minutes in 0.4 M perchloric acid;
   (e) it shows in electrophoresis neutral electric charge with use of 0.01 M phosphate buffer (pH 7) and positive electric charge using 0.2 M formate buffer (pH 2.25);
   (f) it develops color with ninhydrin and fluoresces with fluorescamine;
   (g) it shows maximum absorption substantially at 270 nm, and minimum absorption substantially at 245 nm in water (pH 6.1).

5. An insecticidal composition of claim 2 comprising an amount of the glutamate receptor inhibitor of claim 8 in a concentration of at least 10 ppm and an agriculturally or horticulturally acceptable carrier therefor.

6. A method of combatting insects which comprises contacting said insects with an insecticidal composition of claim 1.

* * * * *